(12) United States Patent
Hendrickson (10) Patent No.: US 6,532,804 B2
(45) Date of Patent: Mar. 18, 2003

(54) METHOD AND APPARATUS FOR ON-LINE MOISTURE ANALYSIS OF A CONCENTRATE

(75) Inventor: David William Hendrickson, Hibbing, MN (US)

(73) Assignee: Cliffs Mining Services Company, Cleveland, OH (US)

( * ) Notice: Subject to any disclaimer, the term of this patent is extended or adjusted under 35 U.S.C. 154(b) by 0 days.

(21) Appl. No.: 09/858,059

(22) Filed: May 15, 2001

(65) Prior Publication Data

US 2002/0170343 A1 Nov. 21, 2002

(51) Int. Cl.[7] .......................... G01N 25/62; G01N 1/00
(52) U.S. Cl. ................ 73/75; 73/76; 73/73; 73/863.11; 73/863.91
(58) Field of Search ................................ 73/863.11, 75, 73/863.91, 864.31, 76, 863.31; 324/694; 209/552, 546; 219/663

(56) References Cited

U.S. PATENT DOCUMENTS

| | | |
|---|---|---|
| 3,621,379 A | 11/1971 | Watson |
| 3,767,900 A | 10/1973 | Chao et al. |
| 3,875,504 A | 4/1975 | Bodycomb, Jr. et al. |
| RE29,132 E | 2/1977 | List et al. |
| 4,131,668 A | 12/1978 | Sasaki et al. |
| 4,198,763 A | 4/1980 | Kurihara |
| 4,228,393 A | 10/1980 | Pile |
| 4,518,699 A | 5/1985 | Bohl |
| 4,683,418 A | 7/1987 | Wagner |
| 4,701,705 A | 10/1987 | Rollwitz |
| 4,750,273 A | 6/1988 | Parkes et al. |
| 4,889,201 A | 12/1989 | Oldendorf et al. |
| 4,955,242 A * | 9/1990 | Long ........................ 73/863.91 |
| 4,964,734 A | 10/1990 | Yoshida et al. |
| 5,072,624 A * | 12/1991 | Montgomery ............ 73/863.91 |
| 5,124,552 A | 6/1992 | Anderson |
| 5,165,180 A | 11/1992 | Ogiri et al. |
| 5,392,659 A * | 2/1995 | Ford, Jr. et al. ......... 73/863.53 |
| 6,089,079 A | 7/2000 | Rosenblum et al. |
| 6,121,782 A | 9/2000 | Adams et al. |

OTHER PUBLICATIONS

Cleveland Cliffs Internal Technical Summary of Robotic Moisture Analyzer System, date unknown. Summary includes photographs of the system and background information.

Phillip Cancilla et al., "On–Line Moisture Determination of Ore Concentrates 'Review of Traditional Methods and Introduction of a Novel Solution,'" 16 pages (2001).

* cited by examiner

Primary Examiner—Hezron Williams
Assistant Examiner—Katina Wilson
(74) Attorney, Agent, or Firm—Watts, Hoffmann, Fisher & Heinke Co.

(57) ABSTRACT

An on-line moisture analyzer and method of analyzing the moisture content of an ore concentrate. A sample conveyor moves a sample of the concentrate to be analyzed to an aluminum pan that receives and holds the sample of the concentrate. A horizontal linear slide having a pneumatic vertical lift mounted to rotary arm is detachably connected to the aluminum pan by gripping fingers that detachably engage the pan. A scale is accessible by the conveyance member for weighing the sample. An oven also accessible by the conveyance member has a door that has a complimentary shape relative to a cross section of the sample container and conveyance member is used for heating the sample. A programmable logic controller controls the conveyance member and the oven door. A data processing unit receives data from the scale and determines a moisture content based on the data.

8 Claims, 8 Drawing Sheets

METHOD AND APPARATUS FOR ON-LINE MOISTURE ANALYSIS OF A CONCENTRATE

TECHNICAL FIELD

The invention relates generally to the field of on-line testing of moisture content of processed material. In particular, the invention relates to an on-line moisture analyzer for testing the moisture content of ore concentrates.

BACKGROUND OF THE INVENTION

The moisture content of material being processed can be an important factor in assuring the quality of final product and in controlling manufacturing parameters to obtain an optimal moisture content. For example, in the iron ore industry raw ore is ground and mixed with water to form a slurry that is processed to remove undesired constituents such as sand. After processing, the slurry is filtered to remove the bulk of the moisture and the resulting "filter cake" is rolled in a drum to form pellets. The filtering process is controlled to produce a filter cake having a desired moisture content and the rolling process is optimized based on filter cake moisture content. The rolling process requires a relatively constant moisture content in the filter cake for proper processing. Deviations from the desired content can compromise the quality of the pellets. Therefore, it is critical to have real time information about the moisture content of the filter cake to achieve consistent high quality pellets.

Numerous techniques have been developed to test the moisture content of filter cakes and other ore concentrates. A reliable and relatively simple way to determine moisture content is to take a sample, weigh the sample, bake the sample or otherwise remove the moisture from the sample, and then weigh the sample again. The difference in the weight of the sample before and after baking corresponds to the amount of moisture that was present in the sample. This weighing technique is typically done manually in a laboratory environment due to the relatively involved process of obtaining, weighing, and baking the sample. Taking the sample to a separate location increases the delay between the taking of the sample and the availability of useful moisture information to process controls. In addition, the introduction of technicians into the measurement process means that human error may affect the accuracy of the results and that measurements can only be taken when a technician is on duty.

Existing on-line testing techniques monitor filter cake characteristics that are related to moisture content. These characteristics include electrical conductivity, dielectric properties, microwave absorption, and radio frequency transmission. Because the characteristics are affected by properties other than moisture content, such as the precise mineral content of the ore or ph of the water, they are unreliable and may only be accurate to about +/−0.50% (industry standard is +/−0.10%). Infra-red reflectance has been used as an indication of moisture content, but this method has proven unsatisfactory in a factory setting because it is susceptible to errors caused by water vapor or reflective surfaces in the optical path. Neutron activation principles have been employed that determine the hydrogen content of the concentrate from which moisture content is inferred. The devices used in this technique are bulky, complex, and require extensive shielding to diffuse the emitted radiation. One other technique involves correlating moisture content to the drag forces exerted on a probe by the concentrate moving on a conveyor. This method depends on a uniform distribution of concentrate on the conveyor, which is not realistic in a manufacturing environment.

SUMMARY OF THE INVENTION

According to the present invention, an apparatus is provided for measuring the moisture content of a concentrate, such as an iron ore concentrate. According to an embodiment of the invention, a sample container receives and holds a sample of the concentrate. A conveyance member has a plurality of conveyance devices that are connected to the sample container that each move the sample container about a single axis. A scale is accessible by the conveyance member for weighing the sample. An oven having an oven door accessible by the conveyance member heats the sample to remove the moisture. A controller controls the conveyance member and the oven and a processing unit receives data from the scale to determine a moisture content based on the data.

In an embodiment, the conveyance member is a sliding carriage, such as a horizontal linear slide, having a rotatable arm for rotating the sample container about an axis of rotation. A pair of opposing fingers apply a gripping force to the sample container and may have at least one pin insertable into the sample container. A pneumatic vertical lift lifts the arm and the arm features a torque limiting brake.

In an exemplary embodiment, the oven door has a complimentary shape relative to a cross section of the sample container and conveyance member and is adapted to open in response to a signal from the controller. The processing unit determines the moisture content of the sample by finding a difference between a first weight of the sample container before the controller causes the conveyance device to move the sample container into the oven and a second weight of the sample container after the controller causes the conveyance device to remove the sample container from the oven. A plow mechanism in communication with the sample container may be provided for distributing the sample in the sample container. According to a feature of the invention a sweeping mechanism removes sample residue from the sample container after the analysis is complete.

DETAILED DESCRIPTION OF THE PREFERRED EMBODIMENT

Figure 1:
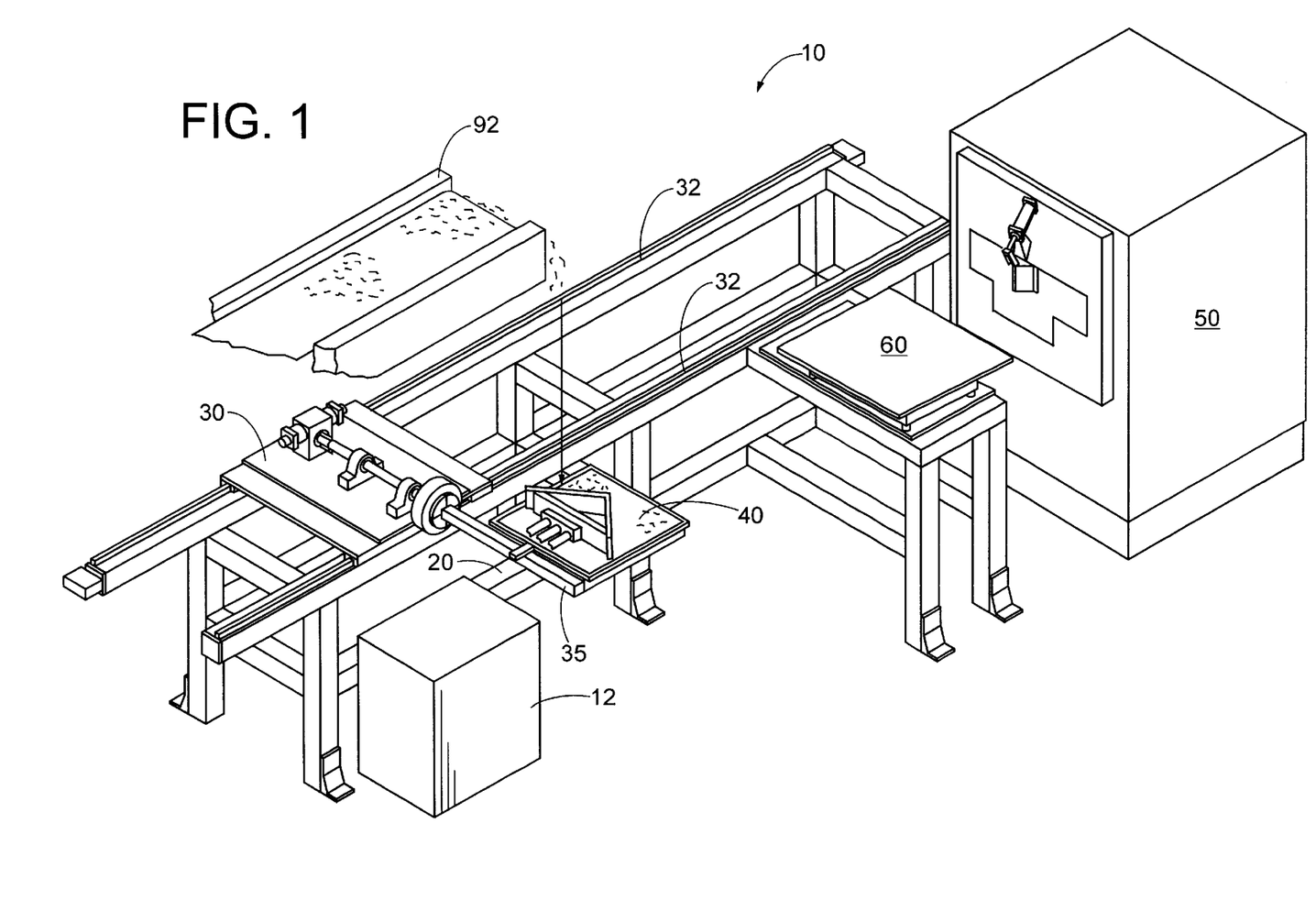
FIG. 1 is a perspective view of an on-line moisture analyzer constructed in accordance with an embodiment of the present invention.

While it is to be understood that practice of the present invention is suitable for moisture testing of any concentrate, the following description will focus on an analyzer constructed in accordance with the present invention adapted for testing of iron ore concentrate. FIG. 1 depicts an on-line moisture content analyzer 10 that can be located in an ore processing facility. Operation of the various components of the analyzer is controlled by a controller shown generally within a housing 12. The analyzer 10 has a supporting structure shown generally as 20 that supports a sliding carriage 30 that rides on rails 32. The supporting structure 20 also supports a laboratory grade scale 60 and a sample plow 41. An oven 50 is located in proximity to the supporting structure and is accessible by a sample holding arm 35 that releasably grips a sample pan 40. The sample pan 40 has a handle 145 with several docking holes (not shown) that engage corresponding pins 132 (FIG. 4) on a gripping member 37. According to the invention, the sliding carriage moves the arm 35 from a sample conveyor 92 (such as a Roach Model 350 SB Conveyor equipped with a variable speed drive motor assembly), where it receives an ore concentrate sample in the pan 40, to the scale 60 where the sample is weighed. After the sample is weighed, the arm 35 moves the sample into the oven 50 for drying and back onto the scale to be reweighed. A processing unit (shown generally within the housing 12) determines the moisture content of the sample by finding the difference between the two weights.

Figure 2:
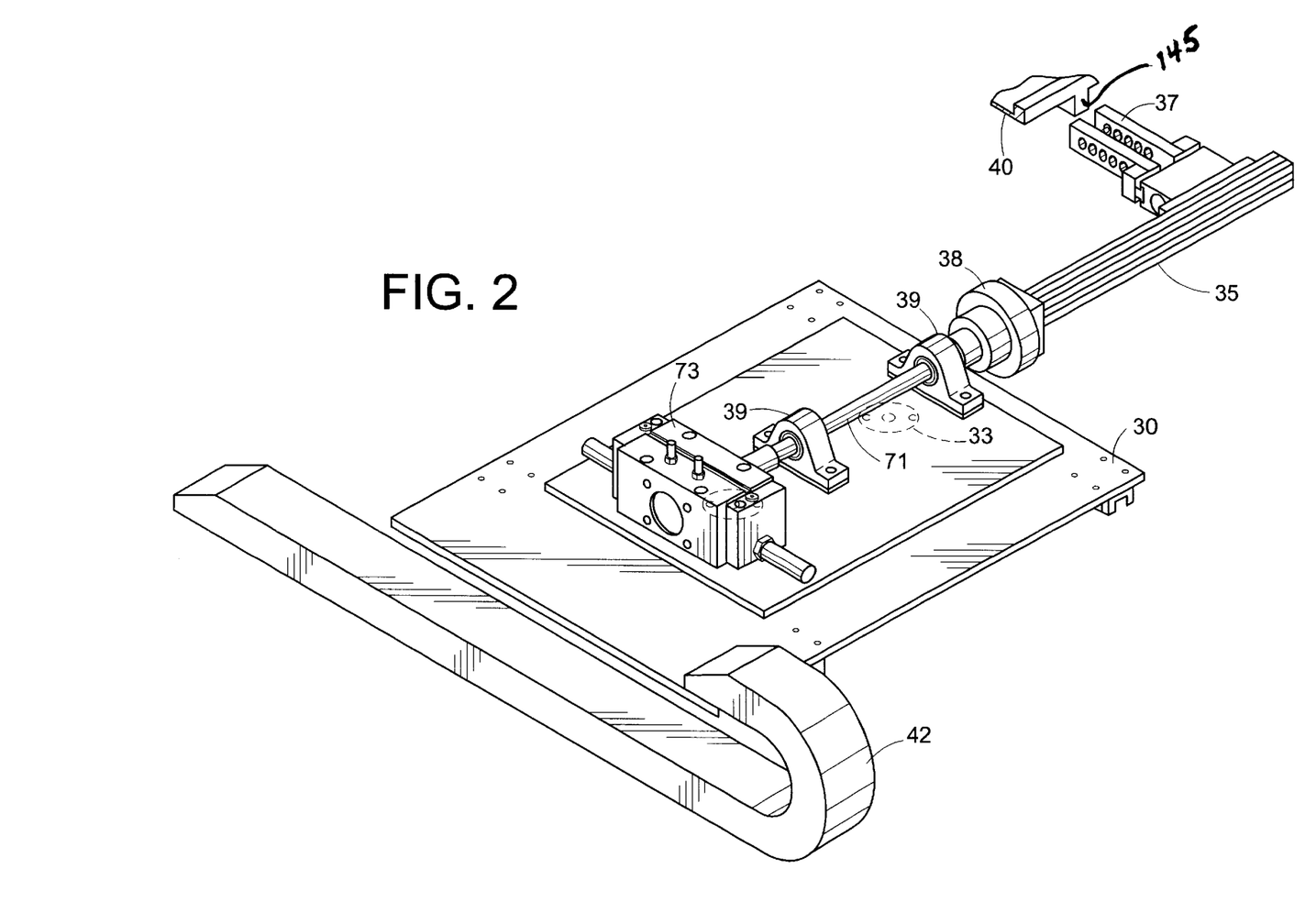
FIG. 2 is an enlarged perspective view of the sliding carriage shown in FIG. 1.
Figure 3:
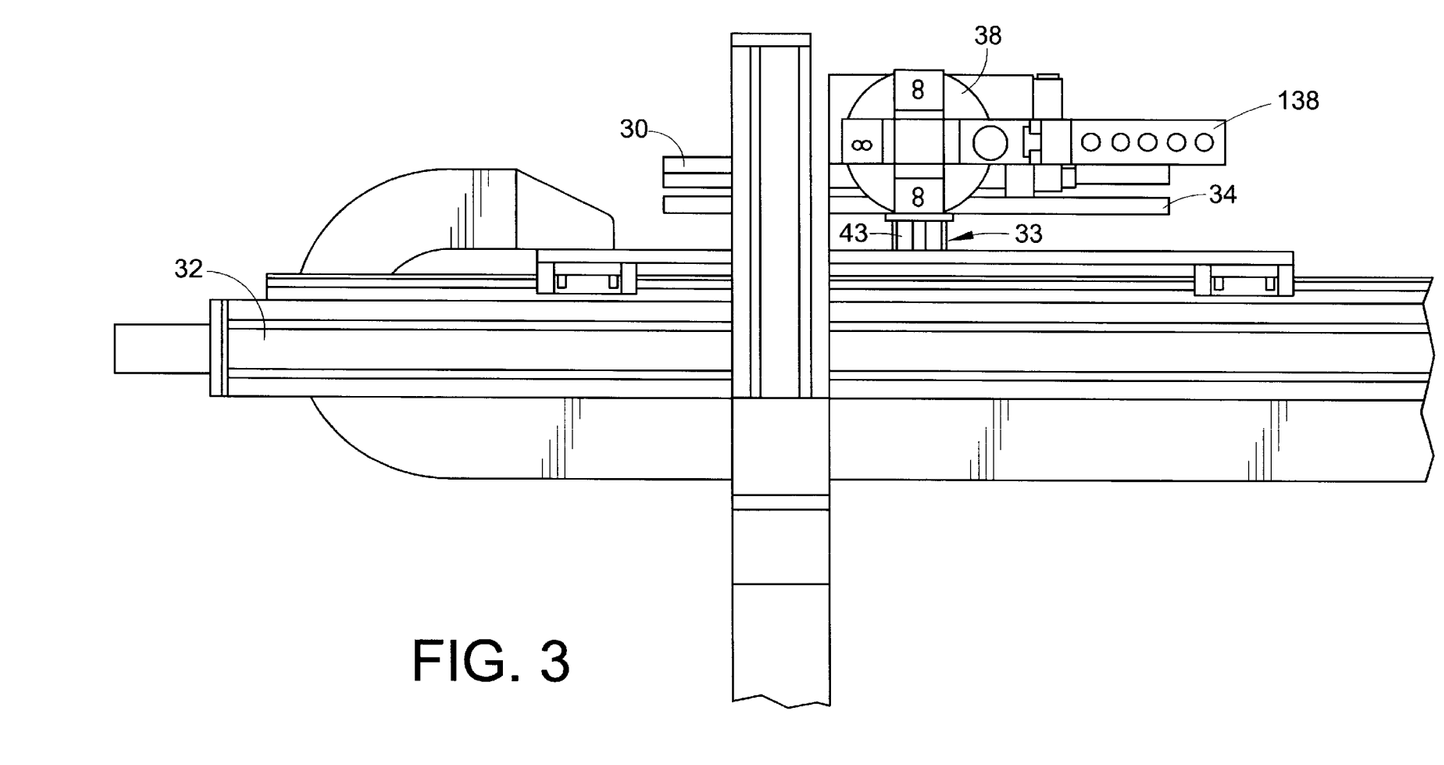
FIG. 3 is a side view of the sliding carriage and support structure shown in FIG. 1.

FIG. 2 depicts the sliding carriage 30 in more detail. The sliding carriage is driven by a GE Fanuc Two Axis Digital Motion Control System. A rotatable shaft 71 is driven by a servo motor (such as PhD Series Ra-S550) located in a housing 73. The shaft 71 is supported by bearing blocks 39 and protrudes into a torque limiting brake 38 (a suitable brake is Applied Robotics Model OS 400). The brake 38 limits the amount of torque that can be output by the arm 35 to prevent damage or injury if the arm encounters an obstruction when it is rotating. The gripping member 37 releasably connects to the handle 145 of the sample pan 40 shown in FIG. 1. A flexible sleeve 42 protects electrical leads that connect to the devices on the carriage 30. FIG. 3 is a side view of the carriage 30 that illustrates a lifting feature of the carriage. A pneumatic lift 33 (such as PhD Model C7550) supports an upper carriage plate 34 on extendable legs 43. The lift has an approximate stroke of about two inches and lifts the upper carriage plate 34 that supports the arm 35 to allow the arm to place the sample pan 40 on the scale.

Figure 4:
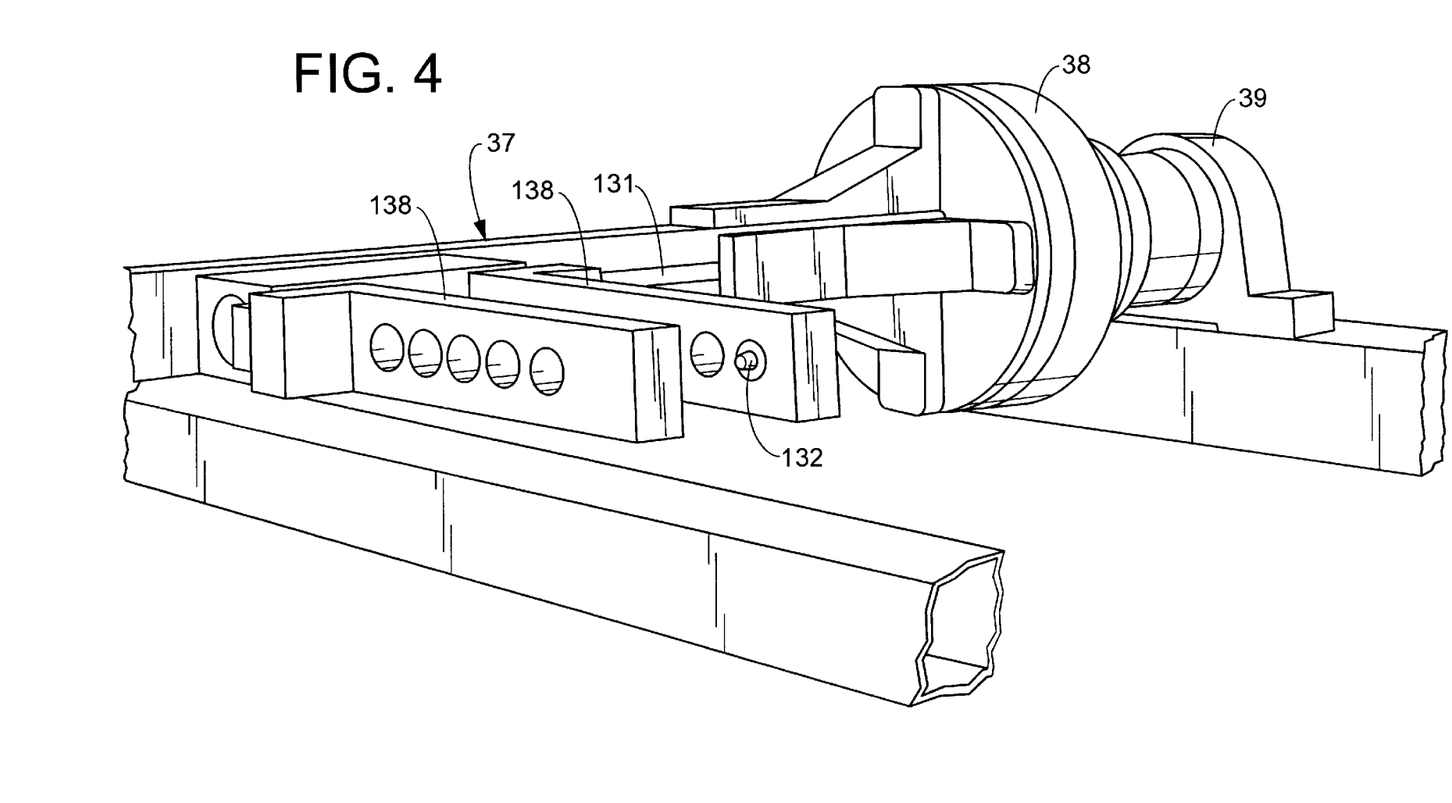
FIG. 4 is a perspective view of the gripping member shown in FIG. 1.
Figure 5:
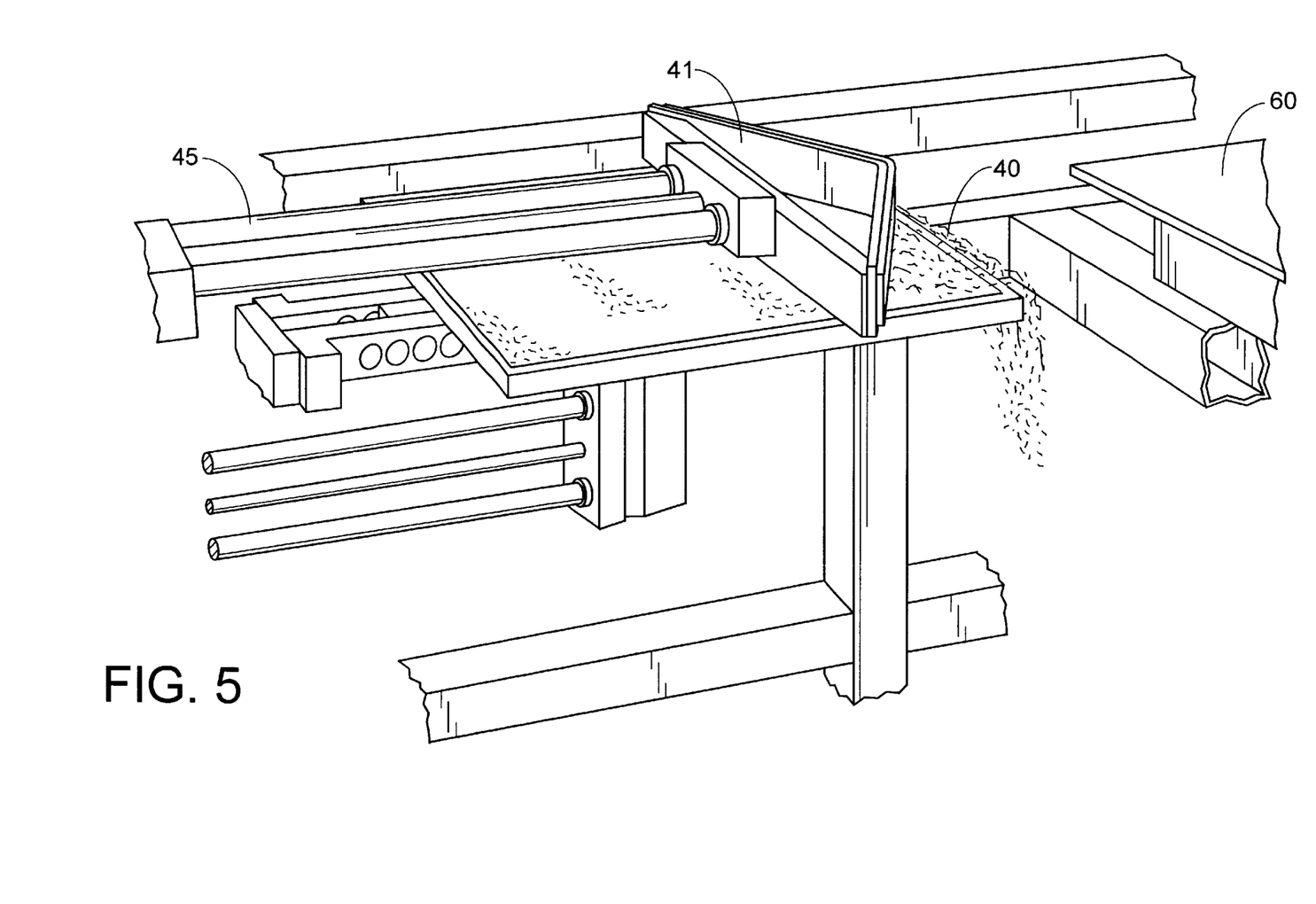
FIG. 5 is an enlarged perspective view of the sample plow shown in FIG. 1.

FIG. 4 illustrates in more detail the gripping member 37. The member features fingers 138, one of which is moveable within a groove 131 in the arm 37. The fingers 138 are pneumatically moved into gripping engagement with corresponding holes (not shown) on a handle 145 of the sample pan 40. FIG. 5 illustrates in more detail the sample plow 41 that is also shown generally in FIG. 1. The sample plow 41 is pneumatically actuated by extendable rods 45. The plow 41 moves across the top of the pan 40 to distribute the ore evenly within the pan 40 to allow for uniform drying in the oven 60.

Figure 6:
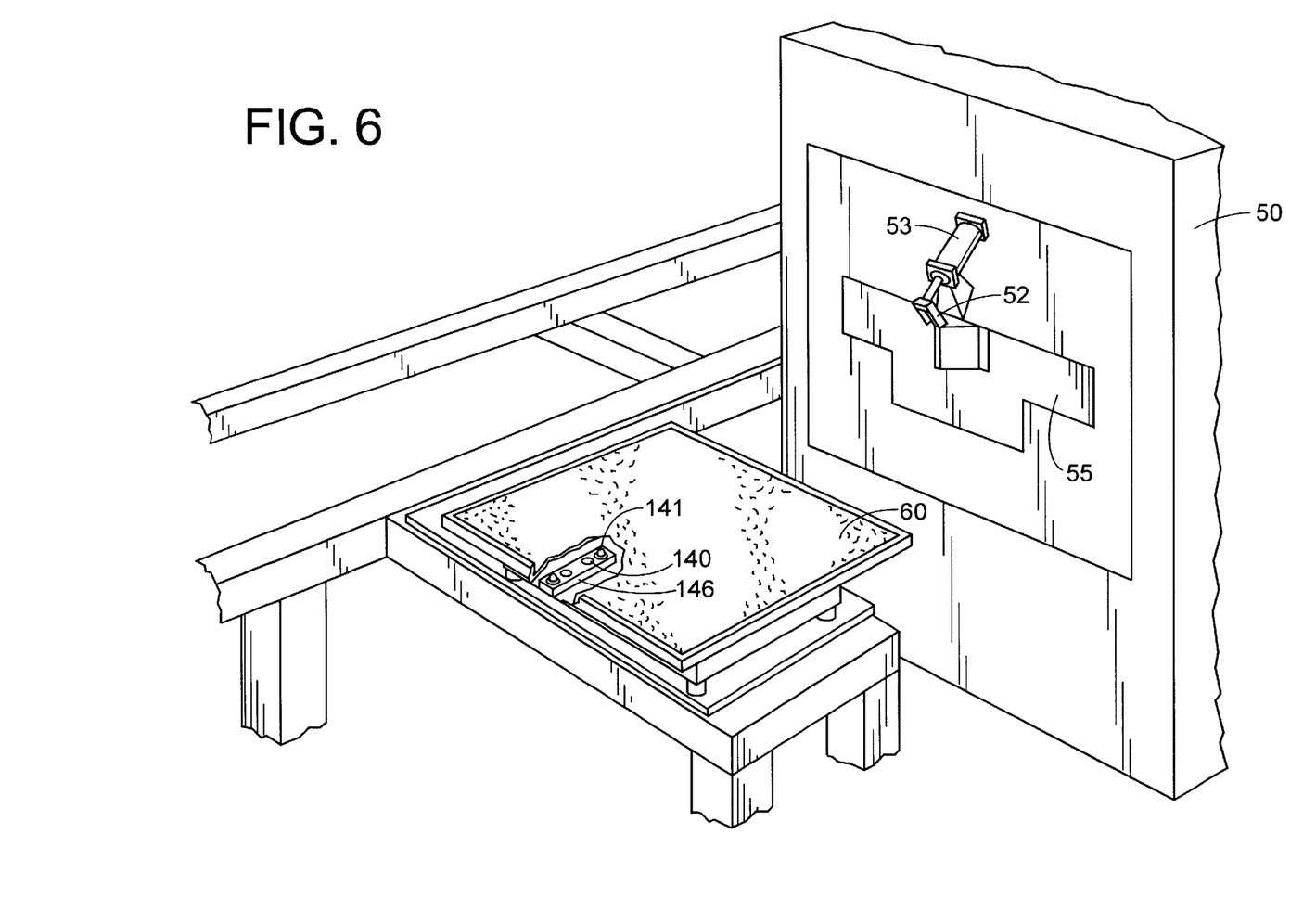
FIG. 6 is an enlarged perspective view of the scale and oven shown in FIG. 1.

FIG. 6 depicts the oven 60 in proximity to the scale 50. A laboratory scale such as Sartorius Model IS-16EDE-S with the docking plate 146 is used to weigh the sample in the pan 40. The scale features a docking plate 146 having pins 141 and holes 140 that engage an underside of the pan 40 to positively located the pan on the scale. The weight of the pan 40 is tared out on the scale periodically so that it does not factor into the moisture determination. A data processing unit, such as an analog input card GE Fanuc Series ALG693, receives sample weights from the scale for use in the calculation of moisture content. A programmable logic controller (located within housing 12) can be used to manipulate the data received from the scale and also to control the operation of the slide, lift, rotary arm, and oven door.

The oven 50 is a convection style oven (such as Despatch Lab Oven Model 142-3) that can quickly heat the sample to temperatures ranging from 32 degrees F. to 500 degrees F. The oven 50 features a notched door 55 shown in a closed position that has a shape adapted to allow close passage into the oven of the gripping member 37 when it is supporting the pan 40. The close fit between the oven door and the gripping member/pan assembly limits the amount of heat that escapes from the oven and minimizes the amount of work necessary to open and close the door. An actuator 53 is connected to the door 55 by a linkage 52 that translates the stroke of the actuator into a pivoting movement of the door between open and closed positions.

Figure 7:
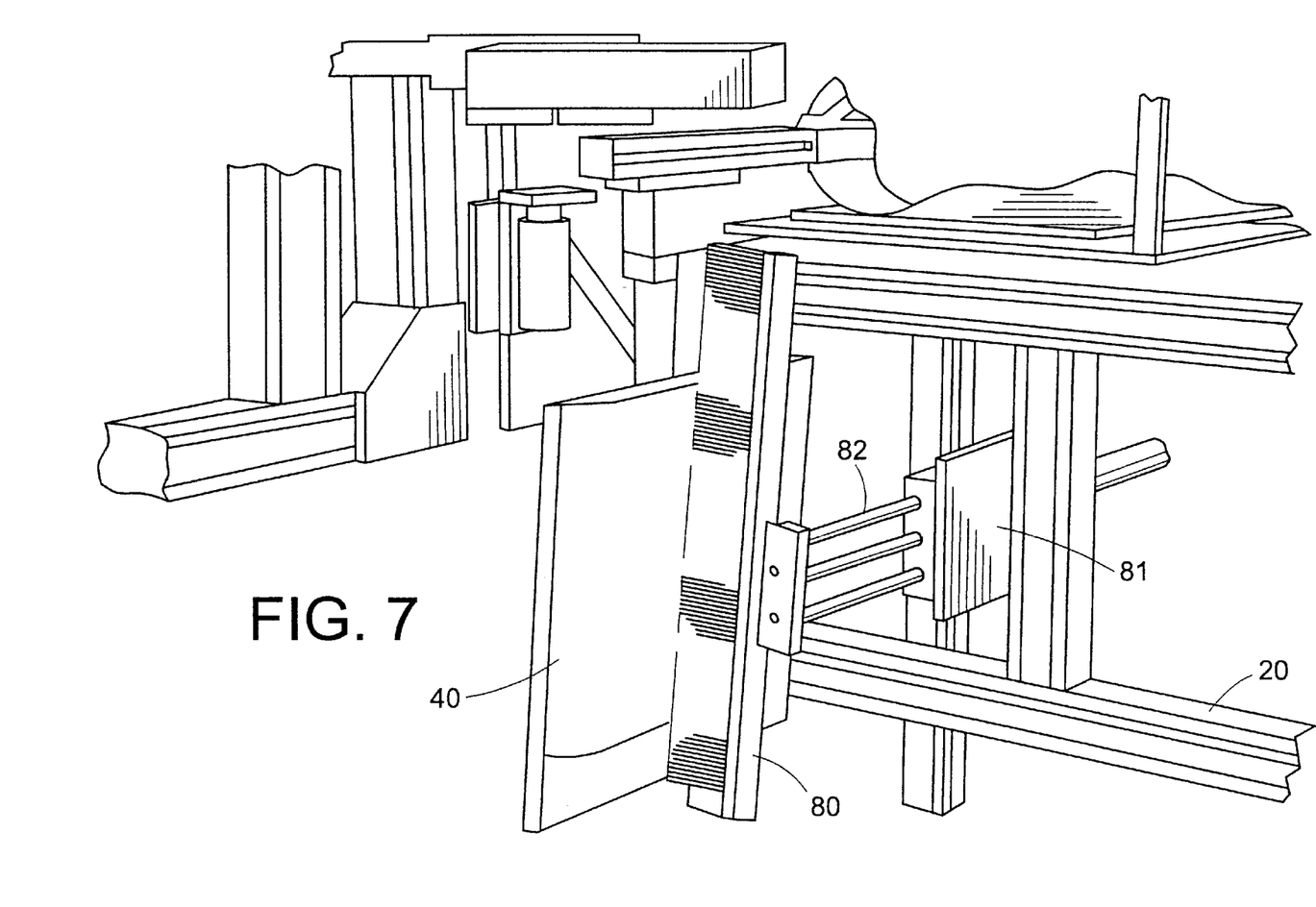
FIG. 7 is a perspective view of a sample pan sweeper constructed according a feature of an embodiment of the present invention.

FIG. 7 depicts a sample pan broom 80 that is supported by the support structure 20. The broom 80 moves across the sample pan 40 to remove any remaining sample material after the arm 35 rotates down to dump the sample (not shown). The broom 80 extends on rods 82 that are actuated by a pneumatic actuator 81. A cooling fan (not shown) is located in proximity to the broom 80 to cool the pan 40 prior to loading of another sample.

Figure 8:
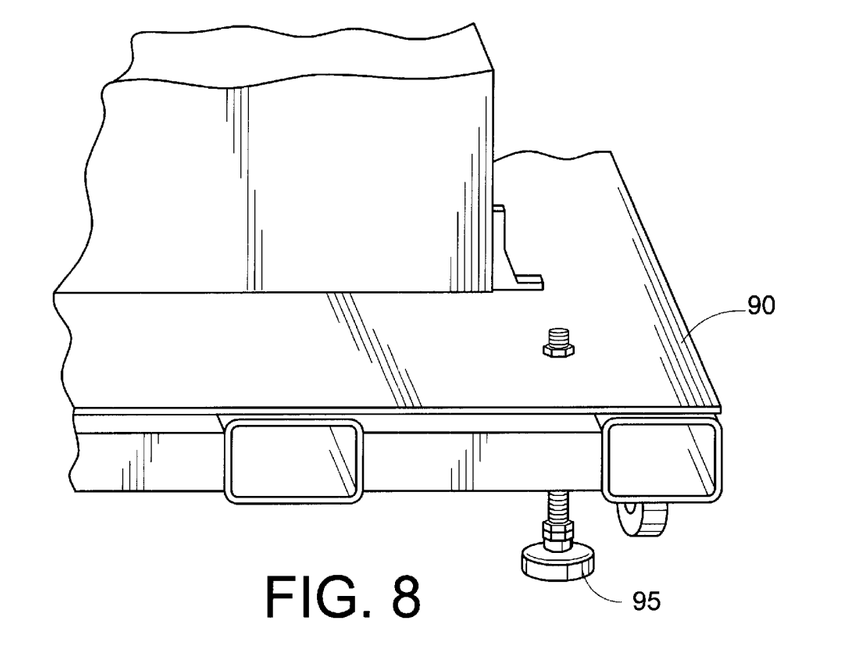
FIG. 8 is a fragmentary view of a support plate for the analyzer shown in FIG. 1.
Figure 9:
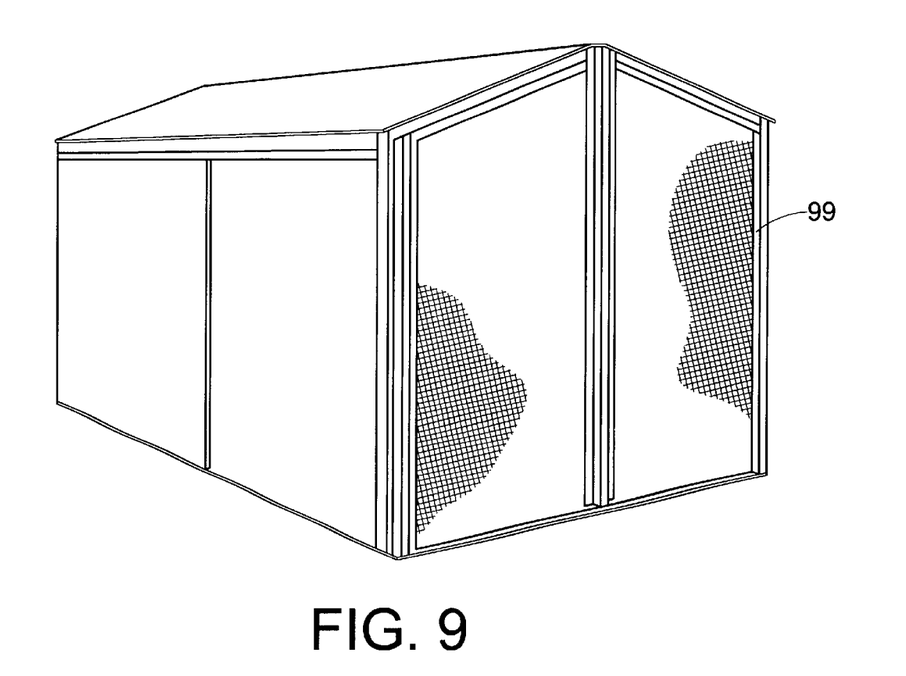
FIG. 9 is a perspective view of an enclosing structure constructed in accordance with the present invention.

FIG. 8 illustrates an analyzer support table 90 on which the support structure 20 and the oven 50 are mounted, making the analyzer 10 a self contained unit that can be moved as a single module. The support table 90 rests on adjustable feet 95 that adjust to level the analyzer 10 and also damp vibrations from the factory floor. FIG. 9 shows a screen enclosure 99 that encloses the analyzer 10 with the exception of an opening (not shown) for the sample conveyor 92 to protect the analyzer from airborne contaminants in the factory.

Referring again to FIG. 1, the operation of the moisture analyzer 10 will be outlined. When the analyzer is set up, the weight of the sample pan 40 is tared out on the scale 60. To begin analyzing ore concentrate, a sample moves down sample conveyor 92. The sample conveyor 92 may be accessible to any number of conveyors to allow for analysis from multiple process locations by the same analyzer 10. The carriage 30 is located at a load location such that the sample pan 40 is beneath the end of the sample conveyor 92. The sample dumps from the conveyor 92 into the sample pan 40 that is held by gripping member 37. The sample plow 41 moves across the pan 40 and distributes the sample to an equal depth throughout the pan. The carriage 30 slides down to the scale 60 and the lift 35 (shown in FIG. 3) lowers the pan 40 onto the scale. The gripping member 37 releases the pan 40. The weight of the sample is sent to the controller.

The gripping member 37 engages the sample pan 40 and the lift 35 raises the pan. The carriage 30 moves to the oven 50. The oven door 55 (FIG. 5) is opened by the door actuator 53 and the carriage moves the gripping member 37 into the oven. The gripping member 37 releases the pan 40, moves out of the oven 50, and the oven door 55 is closed. The sample bakes in the oven 50 until its moisture is removed. This can be accomplished by leaving the sample in the oven a predetermined amount of time or by monitoring the sample and removing it once it is dry. The oven door 55 is opened and the gripping member 37 enters the oven 50 and removes the sample pan 40.

The carriage 30 moves the gripping member 37 to the scale and the sample is again weighed as already described. After the sample has been weighed, the controller calculates the moisture content of the sample. This content is recorded and sent to process controls that depend on the moisture content to effectively process the ore. The carriage 30 moves to a dump station (not shown) and the arm 55 rotates approximately 110 degrees to dump the sample. The broom 80 then removes any sample residue from the pan. The arm 55 returns to its original position and is carried by the carriage 30 back to the load location to receive a new sample. The approximate cycle time of the moisture analyzer 10 is twenty to thirty minutes.

As can be seen from the preceding description, the moisture analyzer in accordance with the present invention provides reliable, accurate, and expeditious on-line analysis of moisture content in a factory floor setting. While the exemplary embodiment of the invention has been described with a degree of particularity, it is the intent that the invention include all modifications and alterations from the disclosed design falling within the spirit or scope of the appended claims.

What is claimed is:

1. An apparatus for measuring the moisture content of a concentrate comprising:
   a) a sample container that receives and holds a sample of the concentrate;
   b) a conveyance member comprising a plurality of conveyance devices connected to the sample container wherein each conveyance device moves the sample container about a single axis;
   c) a scale accessible by the conveyance member for weighing the sample;
   d) an oven comprising an oven door accessible by the conveyance member for heating the sample;
   e) a controller for controlling the conveyance member and the oven;
   f) a processing unit for receiving data from the scale and determining a moisture content based on the data; and
   g) wherein the oven door is adapted to open in response to a signal from the controller.

2. An apparatus for measuring the moisture content of a concentrate comprising:
   a) a sample container that receives and holds a sample of the concentrate;
   b) a conveyance member comprising a plurality of conveyance devices connected to the sample container wherein each conveyance device moves the sample container about a single axis;
   c) a scale accessible by the conveyance member for weighing the sample;
   d) an oven comprising an oven door accessible by the conveyance member for heating the sample;
   e) a controller for controlling the conveyance member and the oven; and
   f) a processing unit for receiving data from the scale and determining a moisture content based on the data wherein the processing unit is adapted to determine the moisture content of the sample by finding a difference between a first weight of the sample container before the controller causes the conveyance member to move the sample container into the oven and a second weight of the sample container after the controller causes the conveyance device to remove the sample container from the oven.

3. An apparatus for measuring the moisture content of a concentrate comprising:
   a) a sample container that receives and holds a sample of the concentrate;
   b) a conveyance member comprising a plurality of conveyance devices connected to the sample container wherein each conveyance device moves the sample container about a single axis;
   c) a scale accessible by the conveyance member for weighing the sample and wherein the scale comprises locating structures that engage the sample container;
   d) an oven comprising an oven door accessible by the conveyance member for heating the sample;
   e) a controller for controlling the conveyance member and the oven; and
   f) a processing unit for receiving data from the scale and determining a moisture content based on the data.

4. An apparatus for measuring the moisture content of a concentrate comprising:
   a) a sample conveyor that moves a sample of the concentrate to be analyzed;
   b) an aluminum pan that receives and holds a sample of the concentrate;
   c) a conveyance member comprising a horizontal linear slide upon which a pneumatic vertical lift is mounted and a rotary arm that is connected to the vertical lift, the conveyance member detachably connected to the aluminum pan by gripping fingers that detachably engage the pan;
   d) a scale accessible by the conveyance member for weighing the sample;
   e) an oven comprising an oven door having a complimentary shape relative to a cross section of the sample container and conveyance member accessible by the conveyance member for heating the sample;
   f) a programmable logic controller for controlling the conveyance member and the oven door; and
   g) a data processing unit for receiving data from the scale and determining a moisture content based on the data.

5. The apparatus of claim 4 wherein the gripping fingers comprise pins that are insertable into the sample pan.

6. The apparatus of claim 4 comprising a torque limiting brake connected to the rotary arm.

7. The apparatus of claim 4 comprising a cooling fan for cooling the sample container.

8. An apparatus for measuring the moisture content of concentrate comprising:
   a) containing means for containing the sample;
   b) conveyance means detachably connected to the containing means for moving the containing means and comprising a plurality of conveyance devices connected to the containing means wherein each conveyance device moves the containing means about a single axis;
   c) weighing means accessible by the manipulation means for weighing the containing means;
   d) heating means accessible by the conveyance means for heating the containing means;
   e) control means for controlling an operation of the conveyance means and the heating means; and
   f) processing means for receiving data from the weighing means and determining a moisture content based on the data and wherein the processing means is adapted to determine the moisture content of the sample by finding a difference between a first weight of the containing means before the control means causes the conveyance means to move the containing means into the heating means and a second weight of the containing means after the control means causes the conveyance means to remove the containing means form the heating means.

* * * * *